United States Patent [19]
Ortiz

[11] Patent Number: 5,015,209
[45] Date of Patent: May 14, 1991

[54] TOOTH FAIRY DOLL

[76] Inventor: Theresa Ortiz, 95 W. 195th St., Apt. 5F, Bronx, N.Y. 10468

[21] Appl. No.: 573,251

[22] Filed: Aug. 27, 1990

[51] Int. Cl.$^5$ .............................................. A63H 3/20
[52] U.S. Cl. .................................... 446/73; 446/369; 446/372; D21/169
[58] Field of Search ................. 446/369, 372, 73, 330; D21/169; 5/434

[56] References Cited

U.S. PATENT DOCUMENTS

| | | | |
|---|---|---|---|
| D. 239,184 | 3/1976 | Cox | D21/169 |
| D. 255,476 | 6/1980 | Cox | D21/169 |
| D. 286,422 | 10/1986 | Dickerson | D21/169 |
| D. 287,612 | 1/1987 | Tebesceff | D21/169 |
| 2,347,405 | 4/1944 | Ford | 446/369 |
| 4,091,481 | 5/1978 | Redman | 5/434 |
| 4,867,729 | 9/1989 | Weinman | 446/330 |

Primary Examiner—Richard J. Johnson

[57] ABSTRACT

The invention relates to a child-playing toy called the "Tooth Fairy Doll" since its basic structure is molar-shaped with two butterfly-like wings at the side. The top of the molar shape is the head and face of the doll while the two roots of the tooth shape are its legs. To complete the 'tooth fairy' idea, the doll carries two arms with a wand in one, and behind the wings, there is a sack or pouch for the tooth the child has just lost. Overnight, the "Tooth Fairy" takes the tooth out of the sack or pouch and in its place leaves a gift for the child. Fairy-like apparel completes the fantasy.

3 Claims, 2 Drawing Sheets

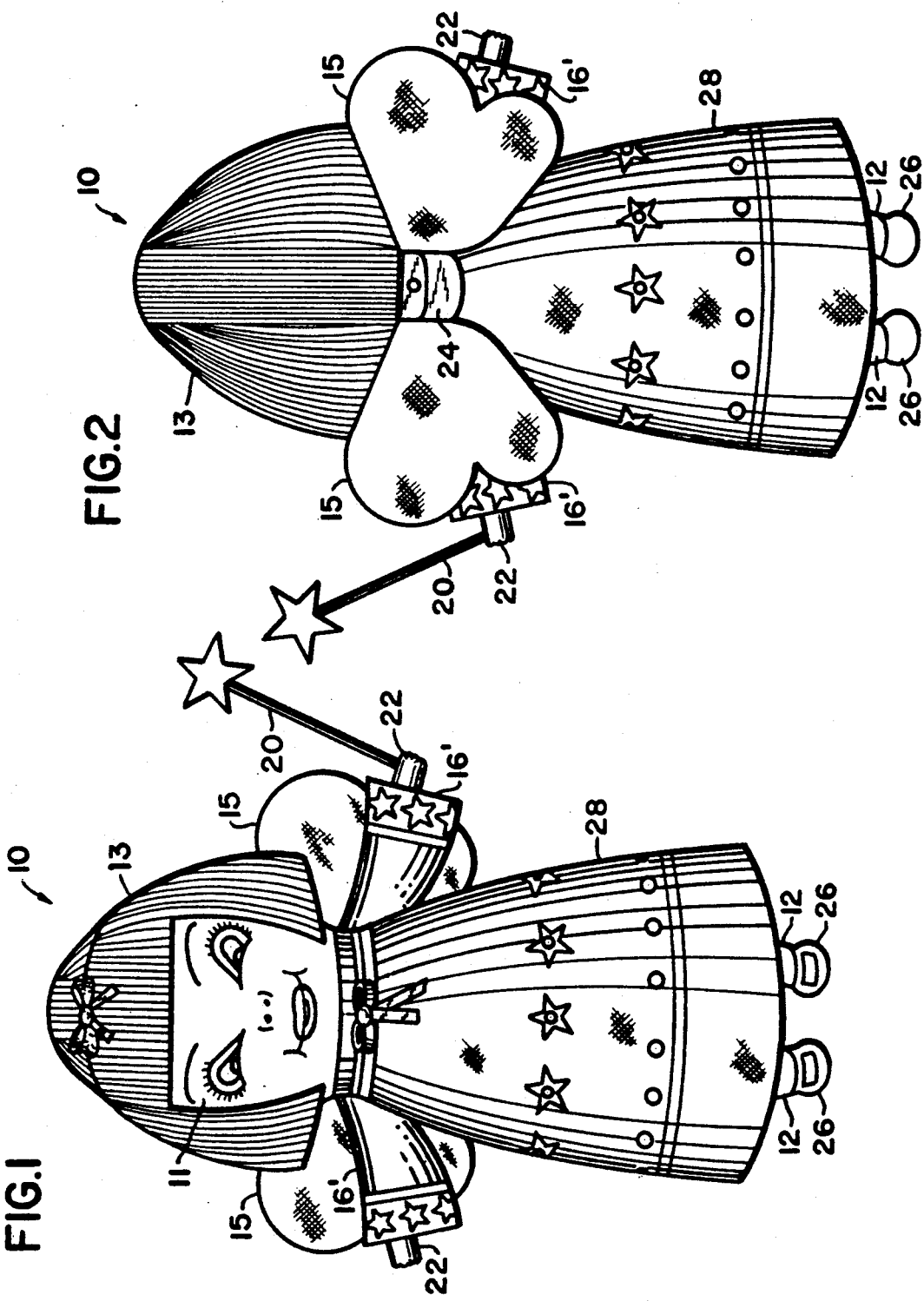

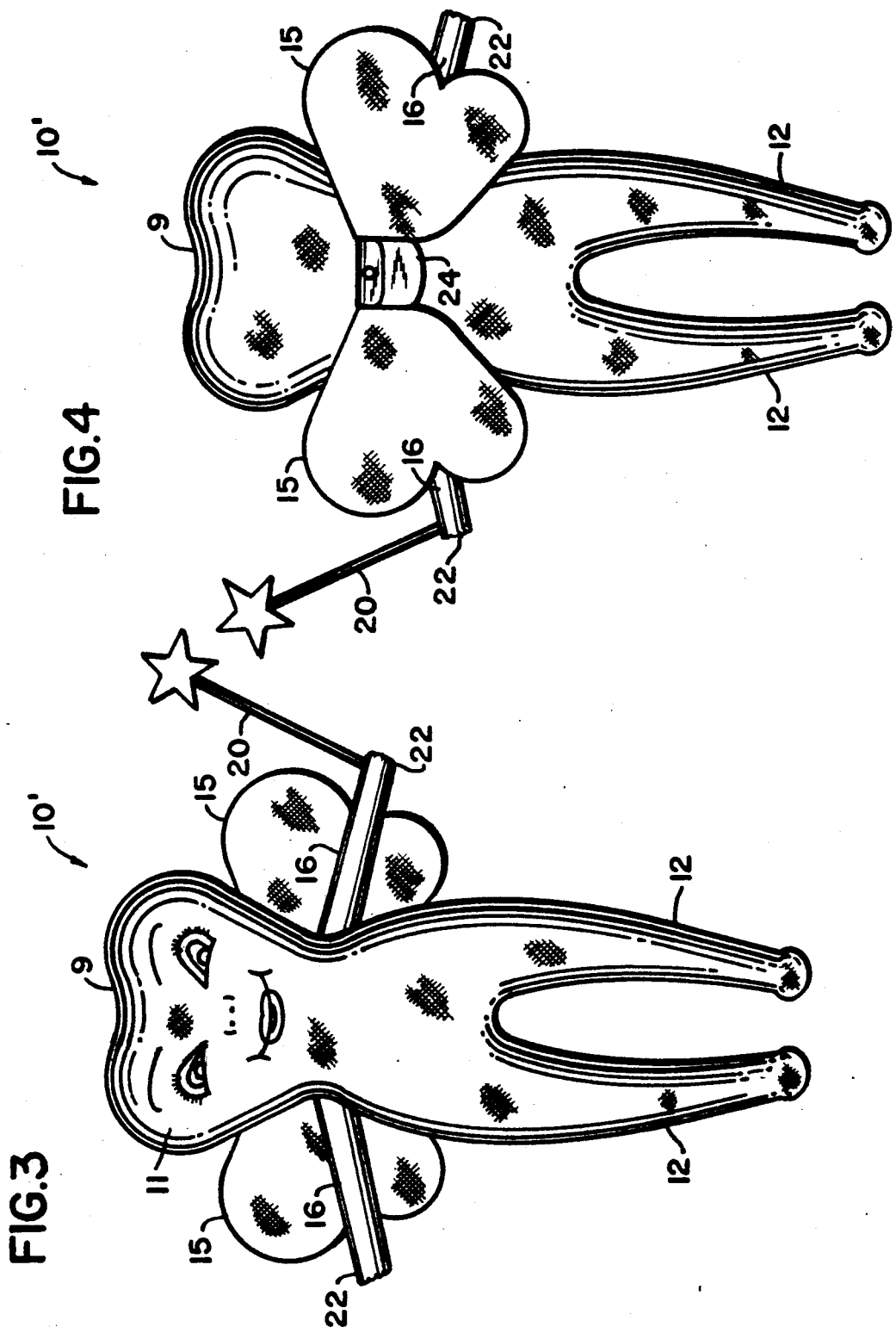

TOOTH FAIRY DOLL

BACKGROUND

The tradition is that a parent hides a tooth just lost by a child, underneath its pillow. That parent then reclaims the tooth while the child is asleep and leaves some 'gift' in its place, on behalf of the 'tooth fairy'. There have been tooth-shaped pillows, but not a doll with wings, pouch and wand as an actual child-playing doll, within the tooth fairy fantasy.

PURPOSE

The purpose of the invention is to extend the tradition so that a parent may hide or place the extracted tooth in the pouch or sack, behind and between the wings of the "Tooth Fairy Doll", and not under the child's pillow, from where it is often difficult to reclaim the tooth while the child is asleep without disturbing or rousing the child. With this invention, a parent may place the lost tooth in the sack or pouch, even in the presence of the child who gets the comfort of playing with a beautiful "Tooth Fairy Doll" and falling asleep with it in the arms, feeling and realizing the 'tooth fairy' fantasy in a more complete and quite intimate way, while the parent may more easily reclaim the item, as the child sleeps, in exchange for a gift, on the 'tooth fairy's' behalf.

DESCRIPTION AND DRAWINGS

Drawings

FIG. 1 gives a front view of the doll showing its winged-tooth shape, the head of the molar being the face while the roots of the molar are the legs of the doll.

FIG. 2 is a rear view that shows the placement of the pouch or sack between, and at the center of, the joined wings.

FIG. 3 shows the fairy-like accessories including dress, underpants, shoes, ribbon and wand. Each of these is needed to complete the fantasy for parent as well as child.

FIG. 4 shows the full look of the doll, frontal view, and completely outfitted as a female "Tooth Fairy Doll".

The invention comprises a doll 10 constructed in the basic configuration of a molar tooth having a crown portion on which is formed a face 11. A pair of tooth roots 12 simulate legs. The doll may be constructed from cloth and stuffed with any suitable stuffing or it may be formed from a suitable plastic.

The doll may be designed as a female figure in which case a dress and hair 13 constructed of rope or other suitable material is provided over the tooth crown or head. If the doll is constructed as a male figure the hair may be omitted thus more fully showing off the molar shape of the doll.

The doll includes two butterfly-like wings 15 secured to its back in an area generally behind its two arms 16. A wand 20 is held in one of the hands. A small sack or pouch 24 made of strong fabric is provided on the back of the doll generally below the wings. Additional fairy-like apparel, including shoes 26, complete the fantasy of a "tooth fairy" as shown on the drawings.

I claim:

1. A doll having arms with a body structured as a molar tooth having a pair of roots simulating legs, said doll including butterfly-like wings secured to the upper back portion of the doll and a wand in one hand, a receptacle disposed at the back of the doll generally where the wings are secured, said receptacle adapted to hold a tooth lost by a child, the doll being clothed with fairy-like apparel whereby to constitute the fantasy of a "tooth fairy doll."

2. The doll of claim 1 wherein the figure is designed as a female including a dress and hair.

3. The doll of claim 1 wherein the figure is designed as a male figure exposing the crown of the molar.

* * * * *